(12) United States Patent
Yanagita

(10) Patent No.: US 7,326,680 B1
(45) Date of Patent: Feb. 5, 2008

(54) UTERINE CONTRACTION INHIBITORS

(75) Inventor: Toshihiko Yanagita, Miyazaki (JP)

(73) Assignee: Shionogi & Co., Ltd. (JP)

( * ) Notice: Subject to any disclaimer, the term of this patent is extended or adjusted under 35 U.S.C. 154(b) by 547 days.

(21) Appl. No.: 10/030,298

(22) PCT Filed: Jun. 23, 2000

(86) PCT No.: PCT/JP00/04167

§ 371 (c)(1),
(2), (4) Date: Dec. 21, 2001

(87) PCT Pub. No.: WO00/78339

PCT Pub. Date: Dec. 28, 2000

(30) Foreign Application Priority Data

Jun. 23, 1999 (JP) .................... 11-177548
Mar. 21, 2000 (JP) ..................... 2000-079171

(51) Int. Cl.
*A61K 38/17* (2006.01)
(52) U.S. Cl. ............... 514/3; 514/4; 530/300; 530/324
(58) Field of Classification Search .......... 514/3, 514/4, 2; 530/303, 304, 324, 399
See application file for complete search history.

(56) References Cited

U.S. PATENT DOCUMENTS 5,639,855 A * 6/1997 Kitamura et al. ............ 530/324
5,910,482 A 6/1999 Yallampalli et al. .......... 514/12

FOREIGN PATENT DOCUMENTS

EP 0 622 458 A2 11/1994
WO 97/34922 * 9/1997

OTHER PUBLICATIONS

Samuelson et al. "Calcitonin Gene-Related Peptide Inhibits Spontaneous Contractions in Human Uterus and Fallopian Tube." Neuroscience Letters, vol. 62 pp. 225-230. 1985.*
Michishita M., et al., "Expression of adrenomedullin in the endometrium of the human uterus." *Obstetrics & Gynecology*, vol. 93, No. 1, Jan. 1999, pp. 66-70.
Eguchi S., et al., "Structure-activity relationship of adrenomedullin, a novel vasodilatory peptide, in cultured rat vascular smooth muscle cells," *Endocrinology*, Baltimore, MD, vol. 135, No. 6, 1994, pp. 2454-2458.
Paul D. Upton et al., "Expression of Adrenomedullin (ADM) and Its Binding Sites in the Rat Uterus: Increased Number of Binding Sites and ADM Messenger Ribonucleic Acid in 20-Day Pregnant Rats Compared with Nonpregnant Rats", Endocrinology (1997), vol. 138, No. 6, pp. 2508-2514.
Brain, Susan D. and Grant, Andrew D., *Vascular Actions of Calcitonin Gene-Related Peptide and Adrenomedullin*, Physiol. Rev., 84, pp. 903-934, 2004.

* cited by examiner

*Primary Examiner*—Anish Gupta
(74) *Attorney, Agent, or Firm*—Fay, Sharpe, Fagan, Minnich & McKee, LLP

(57) ABSTRACT

A composition for inhibiting spontaneous myometrial contraction or bradykinin-induced contraction, comprising adrenomedullin. The composition of the present invention may be used to selectively inhibit spontaneous myometrial contraction or bradykinin-induced contraction to prevent premature labor, prevent miscarriage, arrest parturition prior to cesarean section, or to treat dysmenorrhea.

24 Claims, 7 Drawing Sheets

FIG.1
(A)
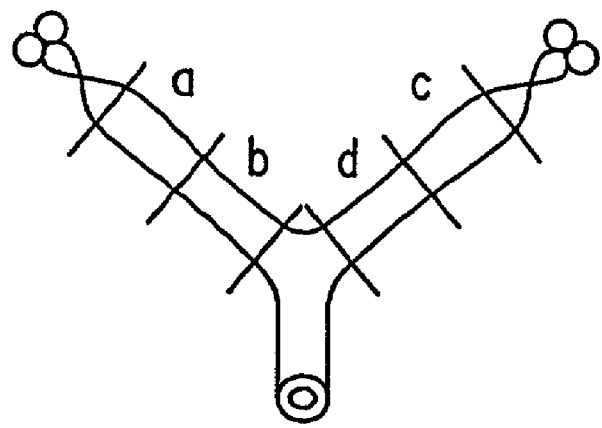
(B)

FIG. 5

```
1                                                        10
Tyr-Arg-Gln-Ser-Met-Asn-Asn-Phe-Gln-Gly-Leu-Arg-Ser-Phe-Gly-
|—RE1—| |———————————— RE2 ————————————| |———RE3———
```

```
       20                                         30
Cys-Arg-Phe-Gly-Thr-Cys-Thr-Val-Gln-Lys-Leu-Ala-His-Gln-Ile-
|———| |—————————————————————————————————RE4————
```

```
                        40
Tyr-Gln-Phe-Thr-Asp-Lys-Asp-Lys-Asp-Asn-Val-Ala-Pro-Arg-Ser-
                                                    —————| |——
———RE5———————————————————————————————————————————|
```

```
       50     52
Lys-Ile-Ser-Pro-Gln-Gly-Tyr-NH2
————RE6————————|
```

UTERINE CONTRACTION INHIBITORS

TECHNICAL FIELD

The present invention relates to a composition for inhibiting spontaneous myometrial contraction or bradykinin-induced contraction, comprising adrenomedullin. More specifically, the present invention relates to a composition for selectively inhibiting spontaneous myometrial contraction or bradykinin-induced contraction, comprising adrenomedullin.

BACKGROUND ART

The management of premature labor is one of the most important issues in the field of obsterics. Premature labor refers to parturition on or after 22 weeks and before 37 weeks of pregnancy, which accounts for 5 to 10% of the total number of childbirths. A neonate delivered by premature labor is called a pronatus, which is frequently a low birth weight infant. Recently, although the care of neonates has progressed significantly, the morbidity and mortality of pronatuses are higher compared to normally delivered neonates. Therefore, it is desired that premature labor is avoided to continue pregnancy as long as possible.

At present, widely used drugs for preventing premature labor include $\beta_2$-adrenergic sympathetic agonist, magnesium sulfate, and indomethacin (a prostaglandin synthesis inhibitor).

Ritodrine, which is a representative $\beta_2$-adrenergic agonist, causes various cardiovascular and metabolic side effects, including tachycardia, elevation of renin secretion, and hyperglycemia in mothers (and hypoglycemia in neonates). Other $\beta_2$-adrenergic agents, such as for example terbutaline and albuterol, cause side effects similar to those of ritodrine.

Magnesium sulfate having a plasma concentration of 4 to 8 mg/dL, which exceeds the therapeutically acceptable range, causes inhibition of cardiac conduction and neuromascular transmission, hypopnea, and cardiac arrest. Therefore, when renal function is impaired, this agent is not preferable.

Indomethacin causes side effects in fetuses, such as for example pulmonary artery hypertension and persistent truncus arteriosus, which are contraindications to large dosage and long-term use of indomethacin.

As described above, currently known drugs for preventing premature labor have various drawbacks. Therefore, there is a demand for a novel drug for preventing premature labor without such drawbacks.

The mechanism of the onset of parturition, i.e., the beginning of pains, has not been yet fully revealed, but it has been suggested that oxytocin, prostaglandin, and the like having a uterine contracting action are involved. Bradykinin has a uterine contracting action similar to oxytocin and prostaglandin, but the physiological or pathophysiological meaning is still unknown. However, bradykinin is inherently an inflammatory mediator, and it has been suggested that there is a possibility that premature labor and miscarriage is caused by abnormally increased bradykinin in the gravid uterus, (Reference 1; List of references are described at the end of this specification). Therefore, if a drug capable of inhibiting spontaneous myometrial contraction or bradykinin-induced myometrial contraction action, or a drug capable of selectively inhibiting spontaneous myometrial contraction or bradykinin-induced contraction action, was especially found, the drug would be expected to be useful not only for preventing premature labor but also for preventing miscarriage and arresting of parturition prior to cesarean section.

Further, such an agent would be expected to be useful in the treatment of dysmenorrhea. This is because dysmenorrhea is characterized by a periodic pain in association with menses during a ovulocycle, and the pain is believed to be derived from uterine contraction and ischemia.

Adrenomedullin (AM), a member of the calcitonin gene-related peptide (CGRP) family, was originally isolated from human pheochromocytoma as a peptide having a hypotensive action (Reference 2). It is known that AM plays multiple roles in a variety of tissues (Reference 3). This suggests that AM has a nonuniform mechanism of action in an organism.

Levels of AM protein or AM mRNA in the female reproductive system (e.g., pituitary posterior lobe [Reference 3] and the uterus [Reference 4]), are as high as those in adrenal medulla. Also, level of circulating AM in maternal blood (Reference 5), and AM and AM mRNA abundance in fetal-placental tissues (Reference 6) and the uterus (Reference 7) were both elevated during normal pregnancy. In gestosis, a complication of pregnancy, the maternal plasma AM level did not alter (Reference 5), or lowered (Reference 8), whereas the AM content in amniotic fluid and umbilical vein were higher, compared to normal pregnancy (Reference 9). However, physiological roles of AM and details of AM function in these fetal and maternal tissues remain elusive.

As to the effect of AM on uterine contraction, it has only been reported that AM inhibited galanin-induced tonic contraction of the uterus at high concentrations of 5 µM or more, and the action of AM was eliminated by CGRP[8-37] (Reference 7). Galanin is a neuropeptide contained in a neuron (CGRP). However, the importance of galanin-induced uterine contraction is not understood at all. AM action is not found at concentrations of the order of nanomolar (nM) or less (which are the concentrations reported in a number of papers as concentrations at which AM can function). It has been only confirmed that AM can function at high concentrations of the order of micromolar (µM) or more. Therefore, it is hardly believed that these effects reflect a physiological function of AM.

The motility of the uterus (contraction/relaxation) is not only regulated by nerves, such as sympathetic nerves and parasympathetic nerves, but also is coordinately regulated by various substances, such as for example CGRP (Reference 10), nitric oxide (NO), oxytocin, and prostaglandin $F_{2\alpha}$ ($PGF_{2\alpha}$: a representative prostaglandin having various actions: elevation of blood pressure; vasoconstriction; promotion of intestine movement; uterine contraction; promotion of regression of corpus luteum; and bronchoconstriction, and used as a parturifacient). Similar to bradykinin described above, substances which can cause abnormal contraction leading to premature labor also influence the motility of the uterus. However, what effect is obtained by AM on spontaneous uterine contraction; the contractility evoked by regulatory factors, such as oxytocin, $PGF_{2\alpha}$ and the like; or bradykinin-induced contraction, is not known at all.

The present invention is intended to solve the above-described problems. The objective of the present invention is to provide a novel agent for inhibiting, preferably selectively inhibiting, spontaneous myometrial contraction or bradykinin-induced contraction.

DISCLOSURE OF THE INVENTION

The inventor found that adrenomedullin, originally identified as a peptide having a hypotentive action, has an action of selectively inhibiting spontaneous myometrial contraction and bradykinin-induced contraction and that the inhibitor action is selective, and based on this finding, completed the present invention.

A composition of the present invention for inhibiting spontaneous myometrial contraction or bradykinin-induced contraction comprises AM. The composition of the present invention may be used for selectively inhibiting spontaneous myometrial contraction or bradykinin-induced contraction, preventing premature labor, preventing miscarriage, arresting parturition prior to cesarean section, and treating dysmenorrhea.

In one embodiment, the AM includes: (a) a petpide comprising an amino acid sequence from Ser in position 13 to Tyr in position 52 of SEQ ID NO: 2 in SEQUENCE LISTING; (b) a peptide comprising an amino acid sequence having one or several amino acid deleted, substituted, or added in the amino acid sequence (a), and having an action of inhibiting myometrial contraction; (c) a petpide comprising an amino acid sequence from Tyr in position 1 to Tyr in position 52 of SEQ ID NO: 2 in SEQUENCE LISTING; (d) a peptide comprising an amino acid sequence having one or several amino acid deleted, substituted, or added in the amino acid sequence (c), and having an action of inhibiting myometrial contraction; (e) a petpide comprising an amino acid sequence from Ala in position −73 to Tyr in position 52 of SEQ ID NO: 2 in SEQUENCE LISTING; (f) a peptide comprising an amino acid sequence having one or several amino acid deleted, substituted, or added in the amino acid sequence (e), and having an action of inhibiting myometrial contraction; (g) a petpide comprising an amino acid sequence from Met in position −94 to Leu in position 91 of SEQ ID NO: 2 in SEQUENCE LISTING; and (h) a peptide comprising an amino acid sequence having one or several amino acid deleted, substituted, or added in the amino acid sequence (g), and having an action of inhibiting myometrial contraction.

In another embodiment, the C-terminus of the AM may be amidated. Gly may be added to the C-terminus of the AM.

In another embodiment, in the AM, Cys in position 16 and Cys in position 21 of SEQ ID NO: 2 in SEQUENCE LISTING may be crosslinked. The crosslink may be a disulfide bond or a —CH$_2$—CH$_2$— bond.

A method of the present invention for preventing premature labor or miscarriage uses a composition comprising AM.

The present invention also provides use of AM in production of a drug for preventing premature labor or miscarriage.

BRIEF DESCRIPTION OF THE DRAWINGS

FIG. 1(A) is a schematic diagram showing a uterus site from which uterine strips were isolated in examples. FIG. 1(B) is a schematic diagram showing the shape of the prepared uterine strips.

FIG. 5 is a diagram showing the amino acid sequence of AM derived from human pheochromocytoma. RE1 to RE6 indicate fragments produced by digesting the amino acid sequence with arginylendopeptidase.

FIGS. 6(a) to 6(e) are representative records from five separate experiments having similar results. *p<0.05, comparison with responses without a drug (one-way analysis of variance); *p<0.05, comparison with AM alone (two-way analysis of variance).

FIGS. 7(a) to 7(e) show representative records from five separate experiments having similar results.

BEST MODE FOR CARRYING OUT THE INVENTION

Figure 2:
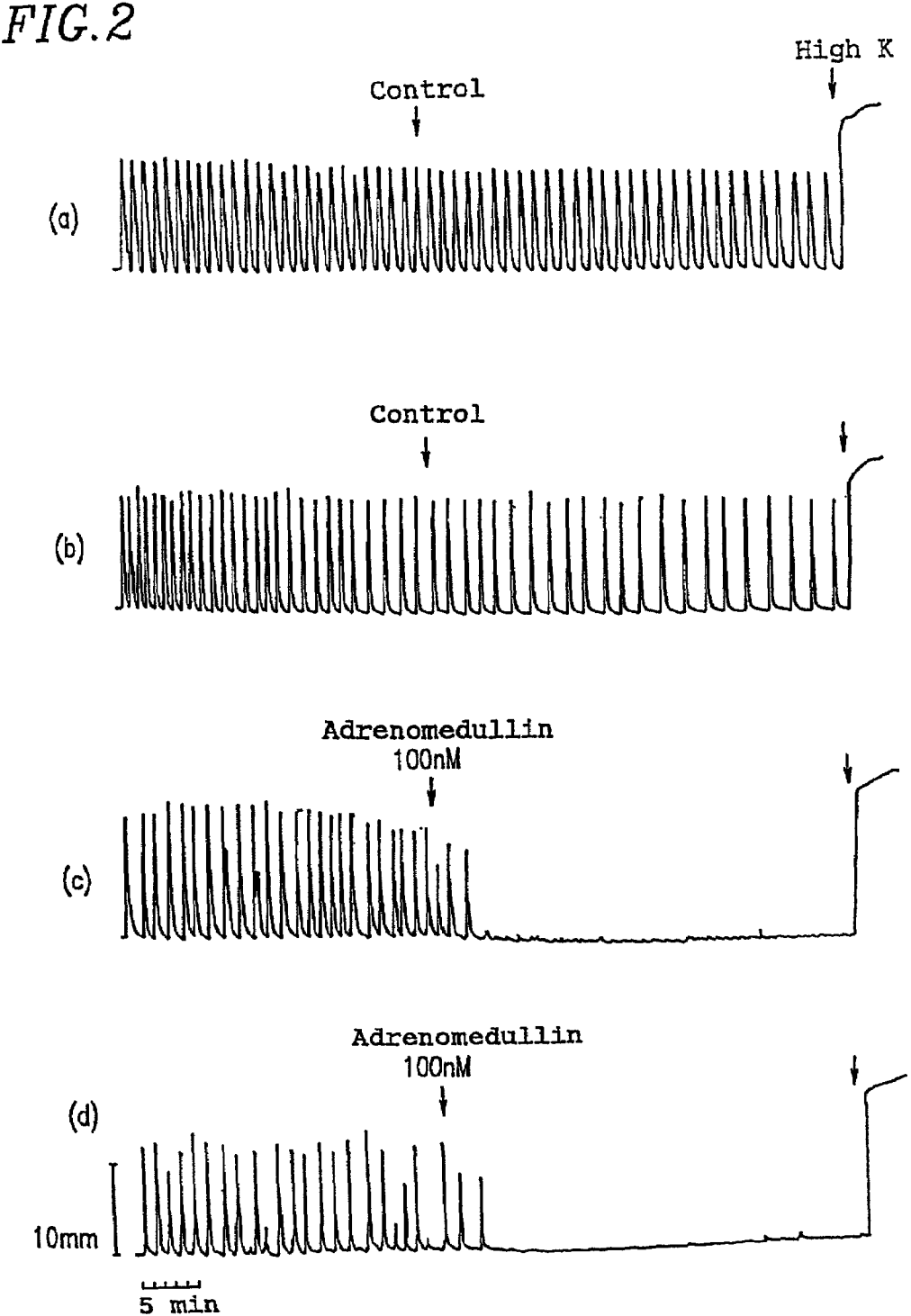
FIG. 2(a) is a graph showing the result of measuring myometrial contraction when distilled water was added to the uterine strip a in FIG. 1(A).
FIG. 2(b) is a graph showing the result of measuring myometrial contraction when distilled water was added to the uterine strip b in FIG. 1(A).
FIG. 2(c) is a graph showing the result of measuring myometrial contraction when 100 nM AM was added to the uterine strip c in FIG. 1(A).
FIG. 2(d) is a graph showing the result of measuring myometrial contraction when 100 nM AM was added to the uterine strip d in FIG. 1(A).

In embodiments of the present invention, protein purification and analysis methods, recombinant DNA techniques, and assays, which are known in the art, are employed unless otherwise specified.

I. Definition

Hereinafter, the terms used herein to explain the present invention will be described.

As described above, "adrenomedullin" is a peptide having a hypotensive action, originally isolated from human pheochromocytoma. The term "adrenomedullin" as used herein is not limited to the particular peptide, but includes peptides having substantial homology with the amino acid sequence of that peptide. Examples of the homologous peptides include species mutants and allelic mutants. Human-derived AM comprises an amino acid sequence from Tyr in position 1 to Tyr in position 52 of SEQ ID NO: 2 in SEQUENCE LISTING. (The peptide consisting of an amino acid sequence from Met in position −94 to Leu in position 91 of SEQ ID NO: 2 in SEQUENCE LISTING is believed to be preproadrenomedullin. The peptide obtained by processing of a signal peptide and consisting of an amino acid sequence from Ala in position −73 to Leu in position 91 of SEQ ID NO: 2 in SEQUENCE LISTING is believed to be proadrenomedullin. The peptide consisting of an amino acid sequence from Ser in position 13 to Tyr in position 52 of SEQ ID NO: 2 in SEQUENCE LISTING is an AM fragment which has been confirmed to have a hypotensive action. AM in any of the above-described forms may be employed in the present invention.) Human-derived AM may be encoded by a polynucleotide sequence from T in position 447 to C in position 602 of SEQ ID NO: 1 in SEQUENCE LISTING. Porcine-derived AM comprises an amino acid sequence from Tyr in position 1 to Tyr in position 52 of SEQ ID NO: 4 in SEQUENCE LISTING. Porcine-derived AM may be encoded by a polynucleotide sequence from T in position 430 to C in position 585 of SEQ ID NO: 3 in SEQUENCE LISTING. Rat-derived AM comprises an amino acid sequence from Tyr in position 1 to Tyr in position 50 of SEQ ID NO: 6 in SEQUENCE LISTING. Rat-derived AM may be encoded by a polynucleotide sequence from T in position 433 to T in position 582 of SEQ ID NO: 5 in SEQUENCE LISTING.

Clearly, human-derived peptides are preferable for human diseases or treatment of a human. However, homologous peptides derived from other mammals may also be employed for some purposes. Further, comparison of human-derived peptides with peptide derived from other mammals is important when an attempt is made to obtain a variant maintaining a desired activity of a human-derived peptide.

AM used in the present invention is not necessarily limited to the above-described sequences, but includes, as subjects, homologous peptides having an amino acid sequence having one or several amino acid deleted, substituted, or added in the above-described sequences and maintaining a desired activity.

Amino acid conservative substitution is one preferable means for obtaining homologous peptides. Conservative substitution representatively includes substitutions conducted within the following groups: glycine, alanine; valine, isoleucine, leucine; aspartic acid, glutamic acid; asparagine, glutamine; serine, threonine; lysine, arginine; and phenylalanine, tyrosine.

The homology between two amino acid sequences is determined by optionally introducing a gap to optimize residue matching. A peptide having an amino acid sequence, which has substantially homology with the amino acid sequence of human AM, has representatively about 60% homology with the amino acid sequence of human AM, preferably at least about 70%, more preferably at least about 80%, and in an especially preferable embodiment, at least about 90% or more. Software for determining homology is easily available.

In the present invention, a peptide is by definition referred to "having an action of inhibiting myometrial contraction" if the degree of spontaneous contraction of uterine muscle is about 90% or less and preferably about 80% or less of the value indicated in the Control sample of Example 1 or if the degree of bradykinin-induced contraction is about 90% or less and preferably about 80% or less of the value indicated in the Control sample of Example 2, when both are measured under substantially the same conditions as those of Example 1 below (the concentration of AM added was 100 nM).

In the present invention, a peptide is by definition referred to as "not inhibiting contraction" if the degree of spontaneous contraction of uterine muscle is about 90% or more and preferably about 95% or more of the value indicated in Control sample of in Example 1; if the degree of bradykinin-induced contraction is about 90% and preferably about 95% or more of the value indicated in the Control sample shown in Example 2; or if degree of contraction induced by oxytocin or prostaglandin $F_{2\alpha}$ is higher about 90% and preferably about 95% or more of a value indicated before the addition of AM in Example 4, when measured respectively under substantially the same conditions as those of Example 1 (the concentration of AM added was 100 nM).

In the present invention, the peptide is referred to as "having an action of selectively inhibiting myometrial contraction" when although spontaneous myometrial contraction or bradykinin-induced contraction is inhibited, myometrial contraction induced by oxytocin and prostaglandin $F_{2\alpha}$ is not inhibited.

The C-terminus of a peptide used in the present invention may or may not be amidated. "Amidation of C-terminus" refers to one of modification reactions of a peptide, in which the COOH group of the C-terminal amino acid of a peptide is changed to the form of $CONH_2$. A number of biologically active peptides functioning in vivo are first biosynthesized as a precursor protein having a larger molecular weight. The precursor protein is then matured by a modification reaction such as for example the amidation of the C-terminus. The amidation is conducted by a C-terminal amidating enzyme acting on the precursor protein. The precursor protein always includes a Gly residue on the C-terminal side of a residue to be amidated, which is frequently followed by a basic amino acid sequence pair, such as for example Lys-Arg or Arg-Arg, on the C-terminal side (Reference 11).

II. AM Having an Action of Inhibiting Myometrial Contraction

In the present invention, AM is used as an effective component of a composition for inhibiting, preferably selectively inhibiting, spontaneous myometrial condition or bradykinin-induced contraction. AM is also used as an effective component for producing a drug for preventing premature labor or miscarriage. AM may be those isolated from naturally-occurring sources, those produced using recombinant DNA techniques, or those chemically synthesized.

When AM is isolated from naturally-occurring sources, purification may be conducted, for example, in the following way. For example, firstly human pheochromocytoma is pulverized to obtain a crude extract, followed by various chromatography techniques so that adenomodullin may be purified. In this case, by monitoring an increase in the cAMP activity of platelets, a fraction containing AM of interest can be obtained. Methods for isolation and purification of AM are described in Japanese Laid-Open Publication No. 7-196693.

When AM is produced using recombinant DNA techniques, the DNA sequence encoding a peptide of interest is expressed using various recombinant systems. Construction of expression vectors and preparation of transformants having appropriate DNA sequences are conducted by methods known in the art. Expression may be conducted using prokaryote systems or eukaryote systems.

Prokaryote hosts used include *E. coli, bacillus,* and other bacteria. For such prokaryote hosts, plasmid vectors having replication sites and control sequences compatible with the hosts are used. For example, *E. coli* is typically transformed with a derivative of pBR322 which is a plasmid derived from *E. coli*. In this case, the control sequence herein includes a promoter for initiation of transcription, an operator if necessary, and a ribosome binding site. Such a control sequence includes generally used promoters such as for example β-lactamase and lactose promoter systems (Reference 12), tryptophan promoters (Reference 13), and $P_L$ promoters derived from λ and N-gene ribosome binding sites (Reference 14).

As an eukaryote host, yeast and mammalian cells may be used, for example. For such an eukaryote host, a plasmid vector having a replication site and a control sequence compatible with the host is used. For example, yeast is transformed with pYEUra3 (Clontech). Other promoter classes useful in a eukaryote host include, for example, promoters for synthesizing a glycolytic enzyme, which include a promoter for 3-phosphoglycerate kinase (Reference 15); a promoter derived from an enolase gene; a promoter derived from a Leu2 gene obtained from YEp13; a promoter derived from metallothionein; an early or late promoter derived from SV40; and other virus promoters such as for example those derived from polyoma virus, adenovirus II, bovine papilloma virus and avian sarcoma virus. A combination of a host cell and an appropriate promoter is known to those skilled in the art and may be appropriately selected if necessary.

A transformant can be obtained by introducing an expression vector into an appropriate host cell. A desired AM can be obtained by culturing the transformant under appropriate conditions.

Chemical synthesis of AM may be conducted within a method known in the art. For example, AM may be synthesized by such a method is a solid phase method on a peptide synthesizer. A C-terminal amidated peptide can be synthesized using a peptide synthesizer by condensing amino acids sequentially from the C-terminal amino acid to the N-terminal amino acid using a benzhydryl amine resin and a standard DCC/HOBt, and cutting out an intended peptide from the resultant peptide resin by a standard cleavage method (trifluoromethanesulfonic acid method).

A C-terminal amidated AM may be obtained by one of the following: a carboxyl group at the C-terminus of the peptide obtained by expression in a host is chemically amidated; or a peptide is prepared so as to have Gly added to the C-terminus of an intended amino acid sequence, and is then allowed to react with the above-mentioned C-terminal amidating enzyme for amidation.

Alternatively, the peptide obtained by adding Gly to the C-terminus of AM may be amidated due to an action of a C-terminal amidating enzyme in vivo as described above.

A disulfide bond can be formed, for example, by oxidizing a peptide by air oxidization or with an appropriate oxidant. The substitution of the disulfide bond can be conducted with a —$CH_2$—$CH_2$— bond by a well-known method (Reference 16). Generally, cleavage in the disulfide bond is avoided by substituting a —$CH_2$—$CH_2$— bond for the disulfide bond, resulting in stabilization of the protein.

Assay methods for action of selectively inhibiting myometrial contraction, which are known in the art, may be used to confirm that the thus-obtained AM has an action of inhibiting, preferably selectively inhibiting, myometrial contraction. Examples of such assay methods include: a method using the uterus of a female rat previously treated with estrogen; a method using the uterus of a virgin female rat in proestrus or estrus; a method using the uterus of a female rat during pregnancy or during or after parturition; and the like. When the uterus of a female rat previously treated with estrogen is used, action of inhibiting myometrial contraction may be assayed, for example, under the following conditions: the uterus is isolated from a female rat to which estrogen (for example, 17β-estradiol) has been administered, and is cut into several parts to obtain uterus fragments. Portions of the uterine strips to which blood vessels are attached are removed to obtain uterine strips. While the resultant uterine strips are immersed in a buffer solution such as for example Ringer's solution, a measurement apparatus, such as for example an isometric transducer and an isotonic transducer, is used to continuously examine myometrial contraction. When a rhythm of uterine muscle in spontaneous contraction become constant, or after bradykinin, oxytocin, or prostaglandin $F_{2\alpha}$ is added to the solution and thereafter a subject peptide is added to the solution, a change in myometrial contraction is examined. Uterine muscle is caused to contract in the presence or absence of the subject peptide to compare levels of contraction, thereby judging the myometrial contraction inhibiting action of the peptide. In this manner, an action of the subject peptide on spontaneous myometrial contraction, or myometrial contraction induced by bradykinin, oxytocin, or prostaglandin $F_{2\alpha}$ is determined. If a subject peptide inhibits spontaneous myometrial contraction and bradykinin-induced contraction, but not oxytocin- or prostaglandin $F_{2\alpha}$-induced myometrial contraction, it is judged that the peptide has a selective myometrial contraction inhibiting action.

III. Preparation of a Composition for Inhibiting Myometrial Contraction

A composition of the present invention comprises, in addition to an effective amount of AM, any excipient known to those skilled in the art. Examples of the excipients include lactose, cornstarch, magnesium stearate, and alum.

The composition of the present invention is prepared in accordance with methods known in the art.

The composition of the present invention may be in any form. The composition of the present invention may be a solid, such as for example a tablet, a pill, a capsule, and a granule; or a liquid, such as for example an aqueous solution and a suspension. When the composition of the present invention is orally administered as a tablet, an excipient, such as for example lactose, cornstarch, and magnesium stearate, may be typically used. When the composition of the present invention is orally administered as a capsule, an excipient, such as for example lactose and dried cornstarch, may be typically used. In order to orally administer AM as an aqueous suspension, the AM may be used in combination with an emulsion or a suspension. The aqueous suspension may optionally contain a sweetner and an aroma chemical. When the composition of the present invention is intramuscularly, intraperitoneally, subcutaneously, or intravenously injected, AM is dissolved in a sterilized solution to prepare a buffer solution which is in turn adjusted into an appropriate pH. When the composition of the present invention is intravenously administered, the composition is preferably isotonic.

The composition of the present invention may be used as an drug for preventing premature labor or miscarriage.

IV. Administration of a Composition for Inhibiting Myometrial Contraction

The composition of the present invention may be administered in the form of a conventional peptide formulation as described in Remington's Pharmaceutical Sciences, Mack Publishing, Easton, Pa. For example, the composition of the present invention may be administered orally, or alternatively parenterally, such as for example intravenous administration, intramuscular injection, intraperitoneal injection, and subcutaneous injection. These peptides may be supplemented into the amniotic fluid. Preferably, these peptides may also be administered by injection.

When the composition of the present invention is administered into a human, typically, the dose per day can be appropriately determined by those skilled in the art by taking into consideration a patient's symptoms, severity, individual differences in sensitivity, weight, age, and the like. The composition of the present invention may be administered once a day or several times a day.

Premature labor or miscarriage would be prevented by administration of the composition of the present invention.

EXAMPLES

Hereinafter, action of AM as an drug of the present invention for inhibiting, or preferably selectively inhibiting, spontaneous myometrial contraction or bradykinin-induced contraction will be more specifically described. The present invention is not limited to the following examples. AM used in the examples is a synthesized peptide consisting of an amino acid sequence from Tyr in position 1 to Tyr in position 50 of SEQ ID NO: 6 (available from Peptide Institute, Inc.).

Example 1

Effect of AM on Spontaneous Contraction of the Uterus of a Female Rat

1 µg of 17β-estradiol in 0.2 ml of 30% ethanol was subcutaneously injected to 10 to 12 week old female rats.

On the following day, the rats were sacrificed by hammering their heads. Thereafter, the rats were decapitated, followed by exsanguination. The uteri were isolated from the rats. Each isolated uterus was cut into four fragments a to d (FIG. 1(A)). Portions of each strip to which blood vessels were attached were cut off, thereby obtaining uterine strips (FIG. 1(B)).

The effect of AM on the rat uterus was examined by measuring contractions of the uterine strips using an isotonic transducer TD-112S (manufactured by Nippon Kohden Corporation) where the tension was 1 g.

While the uterine strip was immersed in 30 ml of a modified Krebs-Ringer bicarbonate (KRB) solution with glucose) (hereinafter simply referred to as "modified KRB solution"), the uterine strip was attached to the isotonic transducer. The composition of the modified KRB solution is as follows: 122 mM NaCl, 26 mM $NaHCO_3$, 5 mM KCl, 1 mM $MgSO_4.7H_2O$, 0.03 mM EDTA-2Na, 2.4 mM $CaCl_2$, and 11 mM glucose; pH 7.4).

Myometrial contraction was continuously measured. After spontaneous rhythm of the uterine muscle was confirmed to be constant, 30 µl of $10^{-4}$ M AM (experimental sample) or distilled water (control sample) was added to the respective modified KRB solution with glucose, where the concentration of AM was 100 nM. 30 minutes after the addition of AM or distilled water, 300 µl of 4.5 M KCl was added to make a KCl concentration of 45 mM.

The results are shown in FIGS. 2(a) to 2(d). Here, FIGS. 2(a) to 2(d) correspond to the results obtained by using the uterine strips for the portions a to d in FIGS. 1(A). FIGS. 2(a) and 2(b) show controls. FIGS. 2(c) and 2(d) show the results of the addition of 100 nM AM. Arrows on the left side of each Figure indicate times at which distilled water or AM was added. Arrows on the right side of each Figure indicate the times at which 45 mM KCl was added.

As shown in FIGS. 2(a) and 2(b), spontaneous myometrial contraction was not affected by the addition of distilled water. In the case of the addition of AM, spontaneous myometrial contraction was significantly inhibited (FIGS. 2(c) and 2(d)). Further, since the addition of 45 mM KCl caused strong contradiction both in the control added sample and the AM added sample), it was found that the addition of AM does not affect muscle contraction due to activation of voltage-dependent Ca channels caused by depolarization of smooth muscle cells in the uterus.

Note that when the isometric transducer was used to conduct the same experiment, the same results as above were obtained (data not shown).

Example 2

Concentration-Dependent Effect of AM on the Uterus of a Female Rat

In a manner similar to that of Example 1, uterine strips were prepared, and attached to an isotonic transducer in a modified KRB solution. Myometrial contraction was continuously measured. After it was confirmed that the spontaneous rhythm of uterine muscle became constant, 30 µl of $1\times10^{-6}$, $2\times10^{-6}$, $7\times10^{-6}$, $2\times10^{-5}$, or $7\times10^{-5}$ M AM (experimental samples), or distilled water (control sample) was added to the modified KRB solution at time 0 min (initial addition), 5 min later, 12 min later, 22 min later, and 32 min later, where AM concentrations were 1, 3, 10, 30, and 100 nM, respectively. Thereafter, after 45 minutes from the initial addition of AM or distilled water, 300 µl of 4.5 M KCl was added to the solution to be a KCl concentration of 45 mM.

Figure 3:
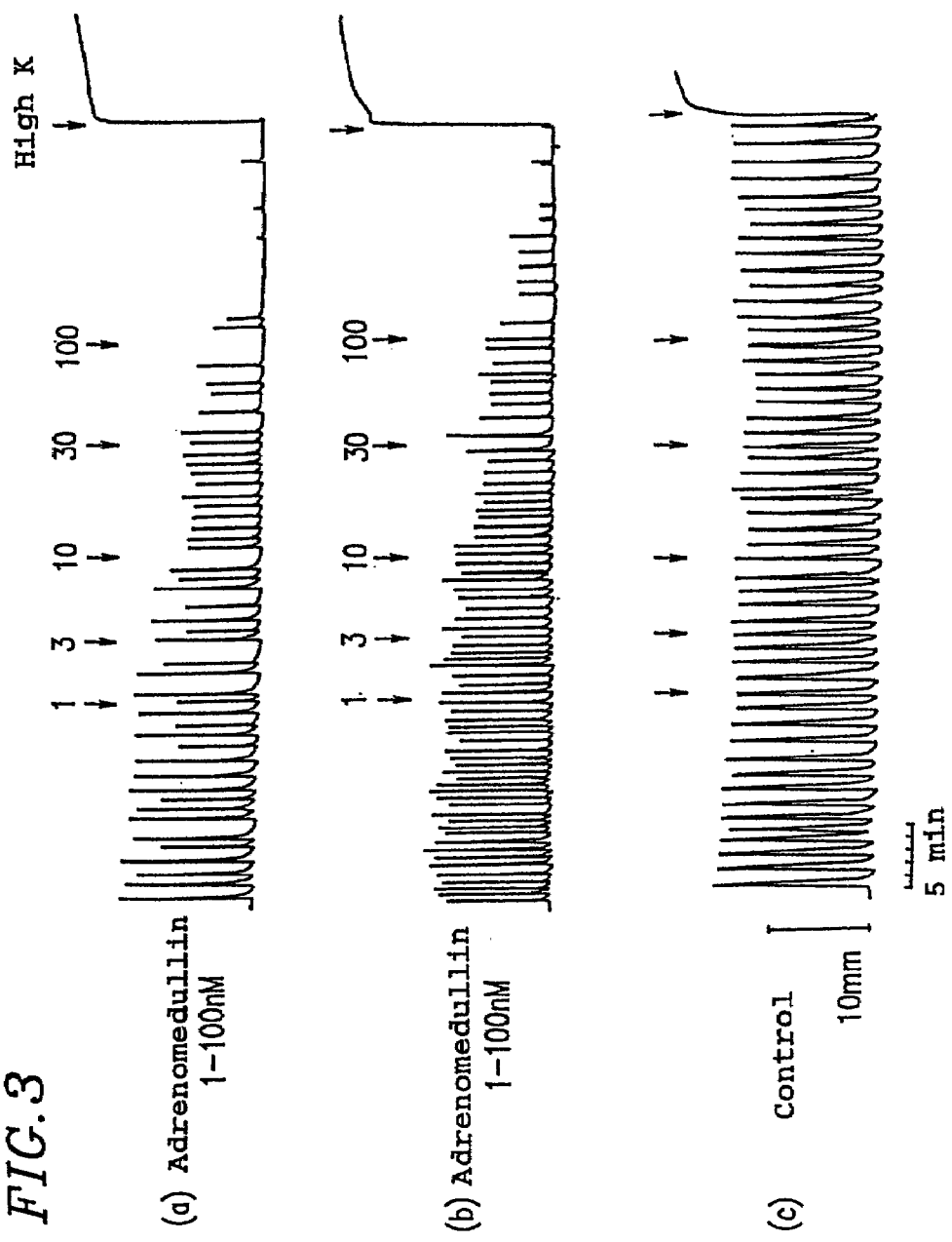
FIG. 3(a) is a graph showing the result of measuring myometrial contraction when 1 to 100 nM AM was added to the uterine strip b in FIG. 1(A).
FIG. 3(b) is a graph showing the result of measuring myometrial contraction when 1 to 100 nM AM was added to the uterine strip c in FIG. 1(A).
FIG. 3(c) is a graph showing the result of measuring myometrial contraction when distilled water was added to the uterine strip d in FIG. 1(A).

The results are shown in FIGS. 3(a) to 3(c). Here, FIGS. 3(a) to 3(c) correspond to the results obtained by using the uterine strips for the portions b to d in FIGS. 1(A), respectively. FIGS. 3(a) and 3(b) show the results of AM addition having various concentrations from 1 to 100 nM. FIG. 3(c) shows the results of the controls. Arrows in each figure indicate times at which AM, distilled water, or KCl was added.

As shown in FIGS. 3(a) and (b), it was found that spontaneous myometrial contraction was inhibited by the addition of AM in a concentration-dependent manner.

Example 3

Inhibition of Bradykinin-Induced Contraction by AM

In a manner similar to that of Example 1, uterine strips were prepared and attached to an isotonic transducer in a modified KRB solution. At the time when 10 nM bradykinin (Peptide Institute, Inc.) was added to the modified KRB solution, myometrial contraction was continuously measured. 20 minutes after the addition of bradykinin, 100 nM AM or distilled water was further added.

Figure 4:
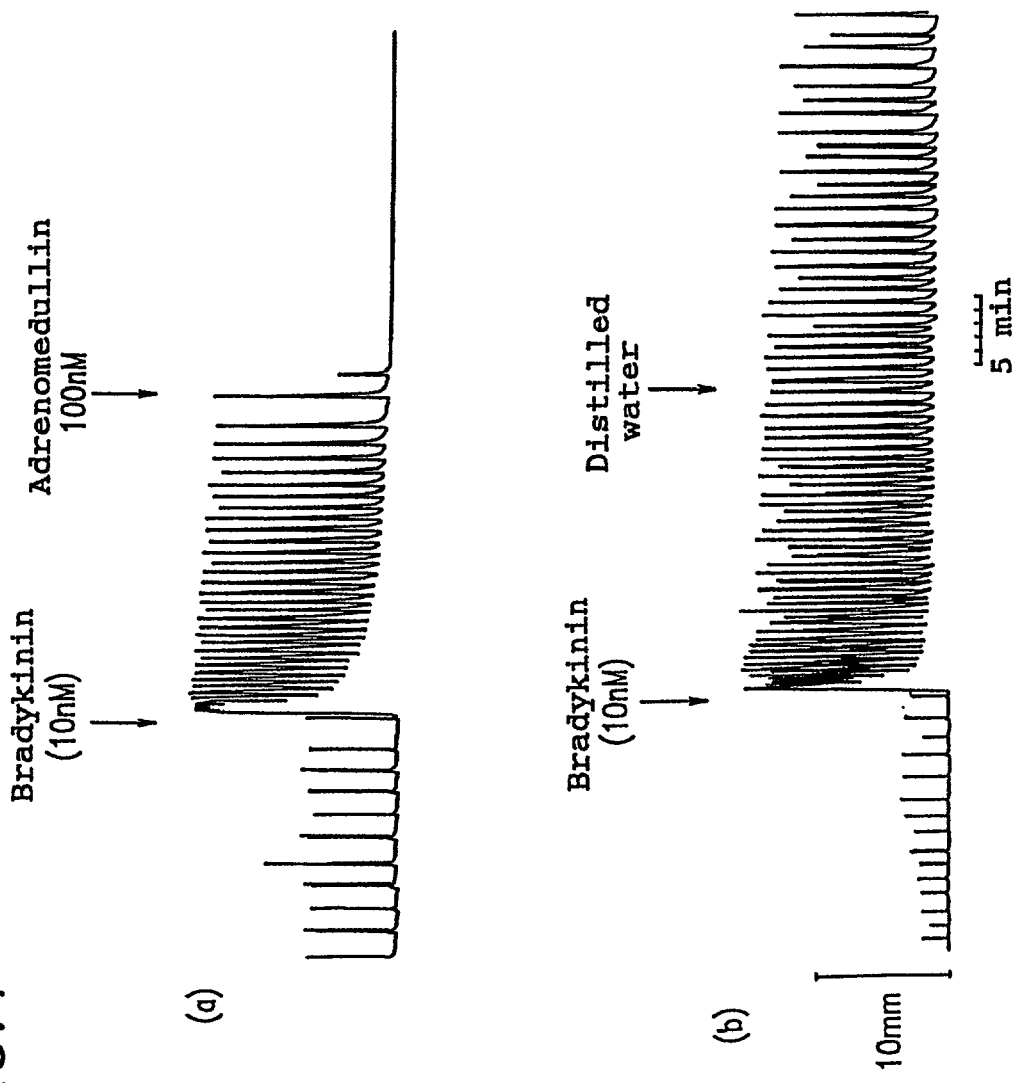
FIG. 4(a) is a graph showing the result of measuring myometrial contraction when bradykinin and then 100 nM AM were added to the uterine strip b in FIG. 1(A).
FIG. 4(b) is a graph showing the result of measuring myometrial contraction when bradykinin and then distilled water were added to the uterine strip b in FIG. 1(A).

The results are shown in FIGS. 4(a) and 4(b). Here, FIGS. 4(a) and 4(b) correspond to the results obtained by using the uterine strips for the portions a and c in FIG. 1(A), respectively. FIG. 4(a) shows the results of addition of 100 nM AM. FIG. 4(b) shows the results of addition of distilled water. Arrows in each figure indicate times at which bradykinin, AM, or distilled water were added.

As shown in FIGS. 4(a) and 4(b), bradykinin-induced contraction was inhibited by the addition of AM.

Example 4

Effect of AM on Contraction Induced by Oxytocin or Prostaglandin $F_{2\alpha}$ 8 to 12 weeks old female rats were used to prepare uterine strips in a manner similar to that of Example 1.

Thereafter, the uterine strip was placed in a tissue chamber filled with 30 ml of a modified KRB solution with aeration of 95% $O_2$/5% $CO_2$ at 37° C. to measure contraction of the uterine strip in a manner similar to that of Example 1. After 40 minutes of equilibrium, the uterine strip was preincubated for 15 minutes in the presence or absence of 1 µM AM[22-52] or 1 µM CGRP[8-37]. Thereafter, AM was added to the modified KRB solution in the tissue chamber to gradually increase the AM concentration from 1 nM to 100 nM, exposing the uterine strip to AM.

In another experiment, rats without injection of 17β-estradiol were used. The effect of 100 nM AM on uterine contraction induced by 10 nM bradykinin, 1 nM oxytocin, or 1 μM PGF$_{2\alpha}$ was tested in the presence or absence of 1 μM AM[22-52] or 1 μM CGRP[8-37].

In all measurements, the uterine strips were eventually contracted due to 45 mM KCl depolarization to confirm responses of the myometrium. The results are shown in FIGS. 6(a) to 6(f) and FIGS. 7(a) to 7(e).

Figure 6:
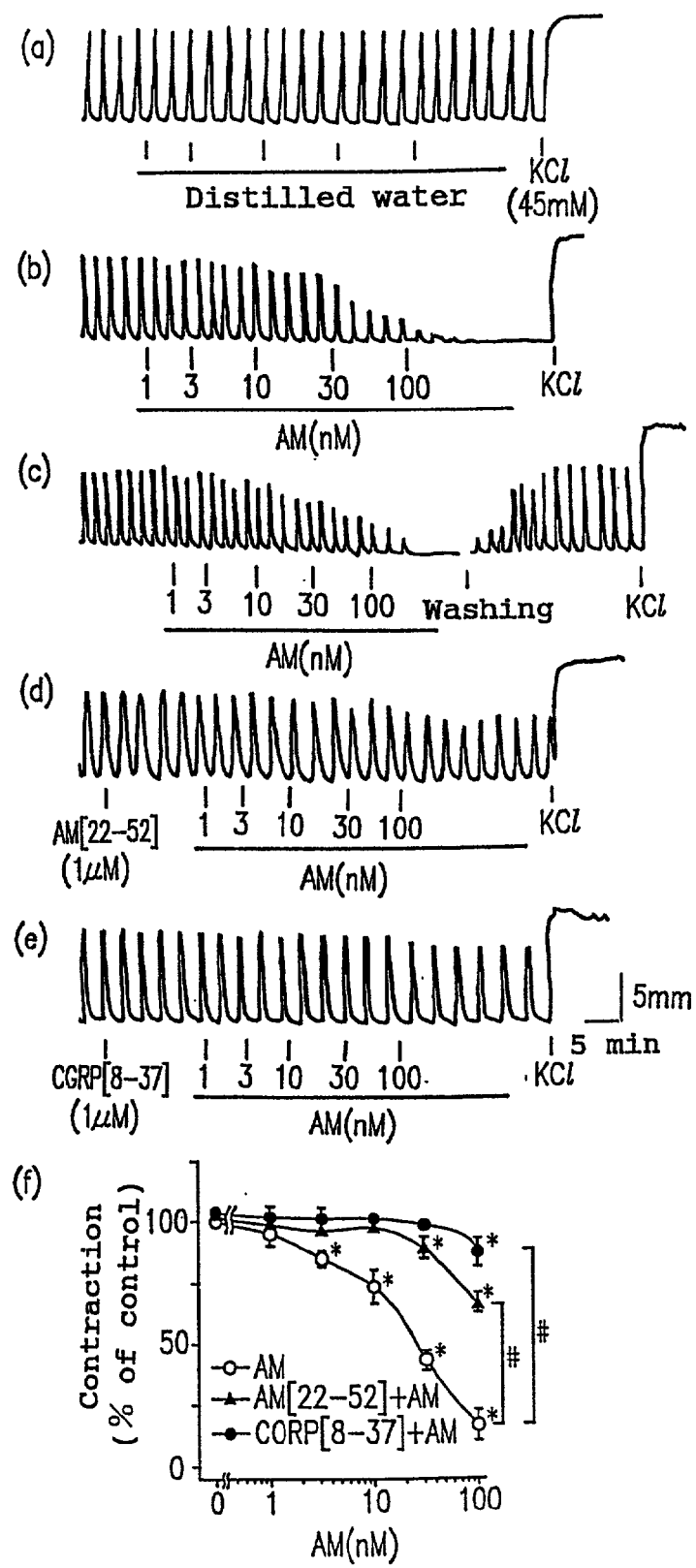
FIG. 6 is a diagram showing concentration-dependent inhibition of spontaneous myometrial contraction of the uterus by AM; and prevention by AM[22-52] or CGRP[8-37].

The uterine strips isolated from the rats treated with 17β-estradiol, a type of estrogen, contracted spontaneously in a rhythmical manner (FIG. 6(a); in this case, distilled water was added instead of an AM solution). AM was added to the chamber so as to gradually increase the concentration (1 to 100 nM). Spontaneous contraction was inhibited in a concentration-dependent manner (IC$_{50}$=23 nM) (FIGS. 6(b) and 6(c)). The inhibitory effect of AM could be reversed by removal of AM by washing out and exchanging the modified KRB solution even when uterine muscle was completely relaxed with 100 nM AM (FIG. 6(c)). The preliminary addition of 1 μM AM[22-52] or 1 μM CGRP[8-37] per se had no effect, but it substantially completely prevents the contraction inhibitory effect of the addition of 1 to 100 nM AM (FIGS. 6(d) and 6(e)). FIG. 6(f) is a graph showing comparison of the results shown in FIGS. 6(b), 6(d), and 6(e).

Figure 7:
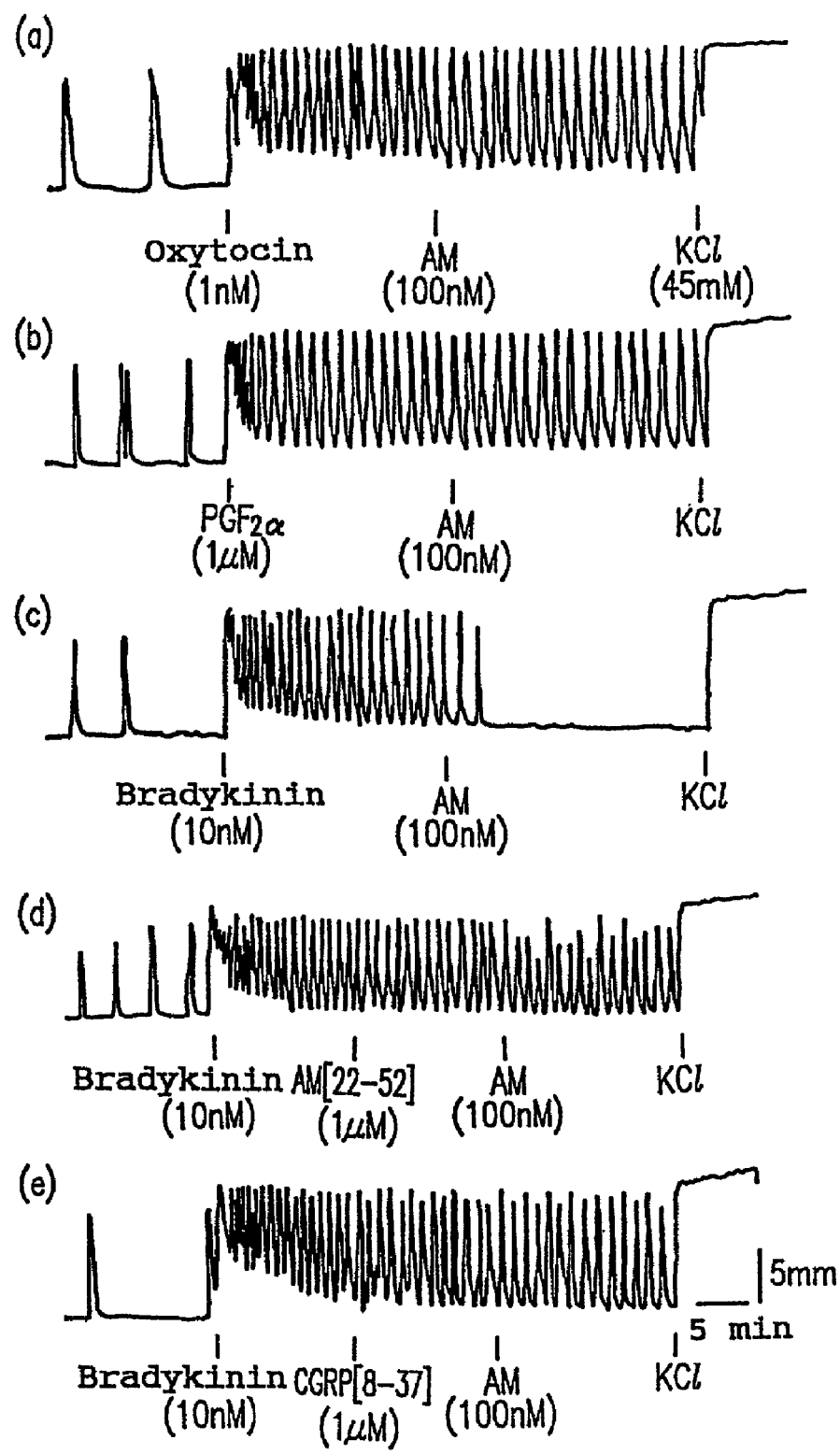
FIG. 7 is a diagram showing inhibition of bradykinin-induced uterine contraction which was caused by AM but not by prevention of oxytocin or PGF$_{2\alpha}$ by AM[22-52] or CGRP[8-37].

When uterine strips were prepared from rats which were not treated with estrogen, these were spontaneously contracted with various intervals and amplitudes. As shown in FIGS. 7(a), 7(b) and 7(c), either 1 nM oxytocin, 1 μM PGF$_{2\alpha}$, or 10 nM bradykinin all significantly stimulated contraction. 100 nM AM substantially had almost no effect on contraction induced by oxytocin (FIG. 7(a)) or PGF$_{2\alpha}$ (FIG. 7(b)). In the other hand, bradykinin-induced contraction was completely blocked by 100 nM AM which is a concentration where spontaneous contraction can be completely inhibited (FIG. 7(c)). The inhibitory effect of AM on bradykinin-induced contraction was eliminated by the preliminary addition of AM[22-52] or CGRP[8-37] (FIGS. 7(d) and 7(e)).

(Discussion of Examples)

To the inventor's knowledge, the above-described examples are the first to demonstrate that AM inhibits autonomous and spontaneous contraction of the uterus of a rat in concentration-dependent and reversible manners. Further, AM inhibited bradykinin-induced contraction, but had no effect on contraction induced by oxytocin or PGF$_{2\alpha}$, or contraction caused by a high K stimulus. This suggests that the AM action does not directly relax smooth muscle of the uterus, and selectively inhibits mechanisms generating spontaneous contraction or bradykinin-induced contraction.

In the above-described examples, the AM uterine contraction inhibiting action was blocked by both AM[22-52] which is an antagonist for an AM receptor and CGRP[8-37] which is an antagonist for a CGRP receptor. Therefore, the AM action is considered to be expressed through the AM receptor and the CGRP receptor. As to that the AM action is blocked by CGRP[8-37], besides the examples, it has been reported that the vasodilatory action of AM was blocked by CGRP[8-37] in the isolated rat mesentery vasculature (Reference 17), that elevation of heart rate and blood pressure due to AM administration into a rat cerebral ventricle was blocked by AM[22-52] or CGRP[8-37] (Reference 18), and the like. Further, it has been reported that in a binding test using the uterus of a rat, AM could display both $^{125}$I-AM binding and $^{125}$I-CGRP binding, i.e., AM could bind to not only a binding site for AM but also a binding site for CGRP (Reference 7). These findings support the results obtained in the examples.

Expression of the AM protein or the AM gene in the uterus is as abundant as the expression level in the suprarenal medulla at which AM was discovered (Reference 7 and 3). It has been reported that in rat and human uteruses, AM is expressed in endometrial tissues rather than smooth muscle tissues of the uterus. Therefore, it is inferred that AM produced in a endometrium acts on uterine smooth muscle as a paracrine factor.

Further, the clinical importance of the uterine contraction inhibiting action of AM will be discussed.

In the pregnant uterus, an expression amount of AM is increased by a factor of about 1.8 to about 4.5 compared to the non-pregnant uterus. An amount of $^{125}$I-AM binding is increased by a factor of about 10, and an amount of $^{125}$I-CGRP binding is increased by a factor of about 4 (Reference 7; Reference 4; and Reference 19). However, it has been reported that the expression of CGRP is reduced to the limit of detection or less (Reference 7). Based on these findings and the results of the examples, i.e., "AM inhibits uterine contraction through the AM receptor and the CGRP receptor", a possibility is suggested that in the pregnant uterus, an increased expression amount of AM inhibits uterine contraction, thereby playing an important role in maintaining pregnancy.

Furthermore, in the examples, AM inhibited bradykinin-induced contraction, but not contraction induced by oxytocin and PGF$_{2\alpha}$. Generally, it is believed that contractions induced by oxytocin and PGF$_{2\alpha}$ play an important role in parturition. While the physiological or pathophysiological importance of bradykinin-induced contractions has not yet been revealed, since bradykinin is inherently an inflammatory mediator locally produced by an inflammation reaction (Reference 20), the possibility has been suggested that an abnormal increase in bradykinin in the pregnant uterus leads to premature labor and miscarriage (Reference 1). Therefore, a possibility is suggested that AM selectively inhibits abnormal contractions due to bradykinin but not contractions during normal parturition due to oxytocin and PGF$_{2\alpha}$, to prevent premature labor and miscarriage and maintain pregnancy.

The above-described results will be briefly described below. In uterine strips isolated from a nonpregnant rat, AM inhibited spontaneous rhythmic contraction in a concentration-dependent manner (IC$_{50}$=23 nM). The inhibitory effect of AM was perfectly blocked by either calcitonin gene-related peptide[8-37] (CGRP[8-37]) which is a putative antagonist for the CGRP receptor or AM[22-52] which is a putative antagonist for the AM receptor. AM also attenuated uterine contraction induced by bradykinin. Bradykinin-induced uterine contraction is blocked by either CGRP[8-37] or AM[22-52]. AM do not have an inhibitory effect or contractile responses induced by oxytocin or prostaglandin F$_{2\alpha}$. These results show that AM selectively inhibits spontaneous myometrial contraction and bradykinin-induced contraction.

REFERENCES

1. Schrey et al., Prostaglandins, Leukotrienes, and Essential Fatty Acids (1992) 45:137-142
2. Kitamura et al., Biochem. Biophys. Res. Commun. (1993) 192:553-560

3. Cameron et al., Endocrinology (1998) 139:2253-2264
4. Makino et al., Eur. J. Pharmacol. (1999) 371:159-167
5. Minegishi et al., Mol. Hum. Reprod. (1999) 5:767-770
6. Dilorio et al., Eur. J. Endocrinol. (1999) 140:201-206
7. Upton et al., Endocrinology (1997) 138:2508-2514
8. Hata et al., Lancet (1997) 350:1600
9. Marinoni et al., Obstet. Gynecol. (1999) 93:964-967
10. Anouar et al., Arch. Pharmacol. (1998) 357:446-453
11. Mizuno, Seikagaku, Vol. 61, No. 12, pp. 1435-1461 (1989)
12. Chang et al., Nature (1977) 198, 1056
13. Goeddel et al., Nucleic Acids Res. (1980) 8:4057
14. Shimatake, Nature (1981) 292:128
15. Hitzeman et al., J. Biol. Chem. (1980) 255:2073
16. O. Keller et al., Helv. Chim. Acta (1974) 57:1253
17. Nuki et al., Biochem. Biophys. Res. Commun. (1993) 196:245-251
18. Saita et al., Am. J. Physiol. (1998) 274:R979-R984
19. Dong et al., Am. J. Obstet. Gynecol. (1998) 179:497-506
20. DeLa et al., Am. J. Physiol. (1991) 260:G213-219

INDUSTRIAL APPLICABILITY

The present invention provides a composition for inhibiting, preferably selectively inhibiting, spontaneous myometrial contraction and bradykinin-induced contraction, comprising AM. This composition is useful in prevention of premature labor and miscarriage, arresting of parturition during cesarean section, and treatment of dysmenorrhea.

The invention claimed is:

1. A method for inhibiting abnormal bradykinin-induced myometrial contraction, comprising administering to the patient in need of treatment, a therapeutically effective amount of adrenomedullin, wherein the adrenomedullin is:
   (a.) a peptide comprising an amino acid sequence from Ser in position 13 to Tyr in position 52 of SEQ ID NO: 2.

2. A method according to claim 1, wherein the C-terminus of the adrenomedullin is amidated.

3. A method according to claim 1, wherein Gly is added to the C-terminus of the adrenomedullin.

4. A method according to claim 1, wherein in the adrenomedullin, Cys in position 16 and Cys in position 21 of SEQ ID NO: 2 are crosslinked.

5. A method according to claim 4, wherein the crosslink is a disulfide bond.

6. A method according to claim 4, wherein the crosslink is a -CH$_2$-CH$_2$- bond.

7. A method for inhibiting abnormal bradykinin-induced myometrial contraction, comprising administering to the patient in need of treatment, a therapeutically effective amount of adrenomedullin, wherein the adrenomedullin is:
   (b.) a peptide comprising an amino acid sequence from Tyr in position 1 to Tyr in position 52 of SEQ ID NO: 2.

8. A method according to claim 7, wherein the C-terminus of the adrenomedullin is amidated.

9. A method according to claim 7, wherein Gly is added to the C-terminus of the adrenomedullin.

10. A method according to claim 7, wherein in the adrenomedullin, Cys in position 16 and Cys in position 21 of SEQ ID NO: 2 are crosslinked.

11. A method according to claim 10, wherein the crosslink is a disulfide bond.

12. A method according to claim 10, wherein the crosslink is a -CH$_2$-CH$_2$- bond.

13. A method for inhibiting abnormal bradykinin-induced myometrial contraction, comprising administering to the patient in need of treatment, a therapeutically effective amount of adrenomedullin, wherein the adrenomedullin is:
   (c.) a peptide comprising an amino acid sequence from Ala in position -73 to Tyr in position 52 of SEQ ID NO: 2.

14. A method according to claim 13, wherein the C-terminus of the adrenomedullin is amidated.

15. A method according to claim 13, wherein Gly is added to the C-terminus of the adrenomedullin.

16. A method according to claim 13, wherein in the adrenomedullin, Cys in position 16 and Cys in position 21 of SEQ ID NO: 2 are crosslinked.

17. A method according to claim 16, wherein the crosslink is a disulfide bond.

18. A method according to claim 16, wherein the crosslink is a -CH$_2$-CH$_2$- bond.

19. A method for inhibiting abnormal bradykinin-induced myometrial contraction, comprising administering to the patient in need of treatment, a therapeutically effective amount of adrenomedullin, wherein the adrenomedullin is:
   (d.) a peptide comprising an amino acid sequence from Met in position -94 to Leu in position 91 of SEQ ID NO: 2.

20. A method according to claim 19, wherein the C-terminus of the adrenomedullin is amidated.

21. A method according to claim 19, wherein Gly is added to the C-terminus of the adrenomedullin.

22. A method according to claim 19, wherein in the adrenomedullin, Cys in position 16 and Cys in position 21 of SEQ ID NO: 2 are crosslinked.

23. A method according to claim 22, wherein the crosslink is a disulfide bond.

24. A method according to claim 22, wherein the crosslink is a —$CH_2$-$CH_2$- bond.

* * * * *

SEQUENCE LISTING

```
<160> NUMBER OF SEQ ID NOS: 6

<210> SEQ ID NO 1
<211> LENGTH: 1457
<212> TYPE: DNA
<213> ORGANISM: Homo sapiens
<220> FEATURE:
<221> NAME/KEY: CDS
<222> LOCATION: (165)..(719)
<221> NAME/KEY: mat peptide
<222> LOCATION: (447)..(602)

<400> SEQUENCE: 1
ggcacgagct ggatagaaca gctcaagcct tgccacttcg ggcttctcac tgcagctggg      60
cttggacttc ggagttttgc cattgccagt gggacgtctg agactttctc cttcaagtac     120
ttggcagatc actctcttag cagggtctgc gcttcgcagc cggg atg aag ctg gtt     176
                                                  Met Lys Leu Val tcc gtc gcc ctg atg tac ctg ggt tcg ctc gcc ttc cta ggc gct gac     224
Ser Val Ala Leu Met Tyr Leu Gly Ser Leu Ala Phe Leu Gly Ala Asp
-90             -85                 -80                 -75 acc gct cgg ttg gat gtc gcg tcg gag ttt cga aag aag tgg aat aag     272
Thr Ala Arg Leu Asp Val Ala Ser Glu Phe Arg Lys Lys Trp Asn Lys
            -70                 -65                 -60 tgg gct ctg agt cgt ggg aag agg gaa ctg cgg atg tcc agc agc tac     320
Trp Ala Leu Ser Arg Gly Lys Arg Glu Leu Arg Met Ser Ser Ser Tyr
        -55                 -50                 -45 ccc acc ggg ctc gct gac gtg aag gcc ggg cct gcc cag acc ctt att     368
Pro Thr Gly Leu Ala Asp Val Lys Ala Gly Pro Ala Gln Thr Leu Ile
    -40                 -35                 -30 cgg ccc cag gac atg aag ggt gcc tct cga agc ccc gaa gac agc agt     416
Arg Pro Gln Asp Met Lys Gly Ala Ser Arg Ser Pro Glu Asp Ser Ser
-25                 -20                 -15 ccg gat gcc gcc cgc atc cga gtc aag cgc tac cgc cag agc atg aac     464
Pro Asp Ala Ala Arg Ile Arg Val Lys Arg Tyr Arg Gln Ser Met Asn
-10                  -5                  -1   1                 5 aac ttc cag ggc ctc cgg agc ttt ggc tgc cgc ttc ggg acg tgc acg     512
Asn Phe Gln Gly Leu Arg Ser Phe Gly Cys Arg Phe Gly Thr Cys Thr
                10                  15                  20 gtg cag aag ctg gca cac cag atc tac cag ttc aca gat aag gac aag     560
Val Gln Lys Leu Ala His Gln Ile Tyr Gln Phe Thr Asp Lys Asp Lys
            25                  30                  35 gac aac gtc gcc ccc agg agc aag atc agc ccc cag ggc tac ggc cgc     608
Asp Asn Val Ala Pro Arg Ser Lys Ile Ser Pro Gln Gly Tyr Gly Arg
        40                  45                  50
```

-continued

```
cgg cgc cgg cgc tcc ctg ccc gag gcc ggc ccg ggt cgg act ctg gtg      656
Arg Arg Arg Arg Ser Leu Pro Glu Ala Gly Pro Gly Arg Thr Leu Val
 55                  60                  65                  70 tct tct aag cca caa gca cac ggg gct cca gcc ccc cgt gga agt          704
Ser Ser Lys Pro Gln Ala His Gly Ala Pro Ala Pro Pro Ser Gly Ser
             75                  80                  85 gct ccc cac ttt ctt taggatttag gcgcccatgg tacaaggaat agtcgcgcaa      759
Ala Pro His Phe Leu
             90 gcatcccgct ggtgcctccc gggacgaagg acttcccgag cggtgtgggg accgggctct    819
gacagccctg cggagaccct gagtccggga ggcaccgtcc ggcggcgagc tctggctttg    879
caagggcccc tccttctggg ggcttcgctt ccttagcctt gctcaggtgc aagtgcccca    939
ggggcgggg tgcagaagaa tccgagtgtt tgccaggctt aaggagagga gaaactgaga    999
aatgaatgct gagaccccg gagcagggt ctgagccaca gccgtgctcg cccacaaact    1059
gatttctcac ggcgtgtcac cccaccaggg cgcaagcctc actattactt gaactttcca    1119
aaacctaaag aggaaaagtg caatgcgtgt tgtacataca gaggtaacta tcaatattta    1179
agtttgttgc tgtcaagatt ttttttgtaa cttcaaatat agagatattt ttgtacgtta    1239
tatattgtat taagggcatt ttaaaagcaa ttatattgtc ctccctatt ttaagacgtg    1299
aatgtctcag cgaggtgtaa agttgttcgc cgcgtggaat gtgagtgtgt ttgtgtgcat    1359
gaaagagaaa gactgattac ctcctgtgtg gaagaaggaa acaccgagtc tctgtataat    1419
ctatttacat aaaatgggtg atatgcgaac agcaaacc                            1457
```

<210> SEQ ID NO 2
<211> LENGTH: 185
<212> TYPE: PRT
<213> ORGANISM: Homo sapiens

<400> SEQUENCE: 2

```
Met Lys Leu Val Ser Val Ala Leu Met Tyr Leu Gly Ser Leu Ala Phe
             -90                 -85                 -80

Leu Gly Ala Asp Thr Ala Arg Leu Asp Val Ala Ser Glu Phe Arg Lys
             -75                 -70                 -65

Lys Trp Asn Lys Trp Ala Leu Ser Arg Gly Lys Arg Glu Leu Arg Met
             -60                 -55                 -50

Ser Ser Ser Tyr Pro Thr Gly Leu Ala Asp Val Lys Ala Gly Pro Ala
             -45                 -40                 -35

Gln Thr Leu Ile Arg Pro Gln Asp Met Lys Gly Ala Ser Arg Ser Pro
-30                  -25                 -20                 -15

Glu Asp Ser Ser Pro Asp Ala Ala Arg Ile Arg Val Lys Arg Tyr Arg
             -10                 -5                  -1   1

Gln Ser Met Asn Asn Phe Gln Gly Leu Arg Ser Phe Gly Cys Arg Phe
             5                    10                  15

Gly Thr Cys Thr Val Gln Lys Leu Ala His Gln Ile Tyr Gln Phe Thr
             20                  25                  30

Asp Lys Asp Lys Asp Asn Val Ala Pro Arg Ser Lys Ile Ser Pro Gln
 35                  40                  45                  50

Gly Tyr Gly Arg Arg Arg Arg Ser Leu Pro Glu Ala Gly Pro Gly
                 55                  60                  65

Arg Thr Leu Val Ser Ser Lys Pro Gln Ala His Gly Ala Pro Ala Pro
             70                  75                  80

Pro Ser Gly Ser Ala Pro His Phe Leu
```

```
                   85                  90

<210> SEQ ID NO 3
<211> LENGTH: 1493
<212> TYPE: DNA
<213> ORGANISM: Sus scrofa
<220> FEATURE:
<221> NAME/KEY: CDS
<222> LOCATION: (148)..(711)
<221> NAME/KEY: mat peptide
<222> LOCATION: (430)..(585)

<400> SEQUENCE: 3
gcggaacagc tcgagccttg ccacctctag tttcttacca cagcttggac gtcgggttt        60 tgccactgcc agaggacgt ctcagacttc atcttcccaa atcttggcag atcacccct       120 tagcagggtc tgcacatctc agccggg atg aag ctg gtt ccc gta gcc ctc atg     174
                              Met Lys Leu Val Pro Val Ala Leu Met
                                                            -90 tac ctg ggc tcg ctc gcc ttc ctg ggc gct gac aca gct cgg ctc gac        222
Tyr Leu Gly Ser Leu Ala Phe Leu Gly Ala Asp Thr Ala Arg Leu Asp
-85                 -80                 -75                 -70 gtg gcg gca gag ttc cga aag aaa tgg aat aag tgg gct cta agt cgt        270
Val Ala Ala Glu Phe Arg Lys Lys Trp Asn Lys Trp Ala Leu Ser Arg
                -65                 -60                 -55 gga aaa aga gaa ctt cgg ctg tcc agc agc tac ccc acc ggg atc gcc        318
Gly Lys Arg Glu Leu Arg Leu Ser Ser Ser Tyr Pro Thr Gly Ile Ala
            -50                 -45                 -40 gac ttg aag gcc ggg cct gcc cag act gtc att cgg ccc cag gat gtg        366
Asp Leu Lys Ala Gly Pro Ala Gln Thr Val Ile Arg Pro Gln Asp Val
        -35                 -30                 -25 aag ggc tcc tct cgc agc ccc cag gcc agc att ccg gat gca gcc cgc        414
Lys Gly Ser Ser Arg Ser Pro Gln Ala Ser Ile Pro Asp Ala Ala Arg
    -20                 -15                 -10 atc cga gtc aag cgc tac cgc cag agt atg aac aac ttc cag ggc ctg        462
Ile Arg Val Lys Arg Tyr Arg Gln Ser Met Asn Asn Phe Gln Gly Leu
-5                  -1   1                5                  10 cgg agc ttc ggc tgt cgc ttt ggg acg tgc acc gtg cag aag ctg gcg        510
Arg Ser Phe Gly Cys Arg Phe Gly Thr Cys Thr Val Gln Lys Leu Ala
                15                  20                  25 cac cag atc tac cag ttc acg gac aaa gac aag gac ggc gtc gcc ccc        558
His Gln Ile Tyr Gln Phe Thr Asp Lys Asp Lys Asp Gly Val Ala Pro
            30                  35                  40 cgg agc aag atc agc ccc cag ggc tac ggc cgc cgg cgc cga cgc tct        606
Arg Ser Lys Ile Ser Pro Gln Gly Tyr Gly Arg Arg Arg Arg Arg Ser
        45                  50                  55 ctg ccc gaa gcc agc ctg ggc cgg act ctg agg tcc cag gag cca cag        654
Leu Pro Glu Ala Ser Leu Gly Arg Thr Leu Arg Ser Gln Glu Pro Gln
60                  65                  70                  75 gcg cac ggg gcc ccg gcc tcc ccg gcg cat caa gtg ctc gcc act ctc        702
Ala His Gly Ala Pro Ala Ser Pro Ala His Gln Val Leu Ala Thr Leu
                80                  85                  90 ttt agg att taggcgccta ctgtggcagc agcgaacagt cgcgcatgca                751
Phe Arg Ile tcatgccggc gcttcctggg gcggggggct tcccggagcc gagcccctca gcggctgggg      811
cccgggcaga gacagcattg agagaccgag agtccgggag gcacagacca gcggcgagcc      871
ctgcattttc aggaacccgt cctgcttgga ggcagtgttc tcttcggctt aatccagccc      931
gggtccccgg gtggggtgg aggtgcaga ggaatccaaa ggagtgtcat ctgccaggct        991
cacggagagg agaaactgcg aagtaaatgc ttagaccccc aggggcaagg gtctgagcca     1051
```

-continued

```
ctgccgtgcc gcccacaaac tgatttctga aggggaataa ccccaacagg gcgcaagcct      1111
cactattact tgaactttcc aaaacctaga gaggaaaagt gcaatgtatg ttgtatataa      1171
agaggtaact atcaatattt aagtttgttg ctgtcaagat ttttttttgt aacttcaaat      1231
atagagatat ttttgtacgt tatatattgt attaagggca ttttaaaaca attgtattgt      1291 tccccteccc tctatttaa tatgtgaatg tctcagcgag gtgtaacatt gtttgctgcg      1351
cgaaatgtga gagtgtgtgt gtgtgtgtgc gtgaaagaga gtctggatgc ctcttgggga      1411
agaagaaaac accatatctg tataatctat ttacataaaa tgggtgatat gcgaagtagc      1471
aaaccaataa actgtctcaa tg                                              1493
```

<210> SEQ ID NO 4
<211> LENGTH: 188
<212> TYPE: PRT
<213> ORGANISM: Sus scrofa

<400> SEQUENCE: 4

```
Met Lys Leu Val Pro Val Ala Leu Met Tyr Leu Gly Ser Leu Ala Phe
            -90                 -85                 -80

Leu Gly Ala Asp Thr Ala Arg Leu Asp Val Ala Ala Glu Phe Arg Lys
        -75                 -70                 -65

Lys Trp Asn Lys Trp Ala Leu Ser Arg Gly Lys Arg Glu Leu Arg Leu
    -60                 -55                 -50

Ser Ser Ser Tyr Pro Thr Gly Ile Ala Asp Leu Lys Ala Gly Pro Ala
    -45                 -40                 -35

Gln Thr Val Ile Arg Pro Gln Asp Val Lys Gly Ser Ser Arg Ser Pro
-30                 -25                 -20                 -15

Gln Ala Ser Ile Pro Asp Ala Ala Arg Ile Arg Val Lys Arg Tyr Arg
            -10                  -5                  -1   1

Gln Ser Met Asn Asn Phe Gln Gly Leu Arg Ser Phe Gly Cys Arg Phe
             5                  10                  15

Gly Thr Cys Thr Val Gln Lys Leu Ala His Gln Ile Tyr Gln Phe Thr
        20                  25                  30

Asp Lys Asp Lys Asp Gly Val Ala Pro Arg Ser Lys Ile Ser Pro Gln
35                  40                  45                  50

Gly Tyr Gly Arg Arg Arg Arg Ser Leu Pro Glu Ala Ser Leu Gly
            55                  60                  65

Arg Thr Leu Arg Ser Gln Glu Pro Gln Ala His Gly Ala Pro Ala Ser
        70                  75                  80

Pro Ala His Gln Val Leu Ala Thr Leu Phe Arg Ile
        85                  90
```

<210> SEQ ID NO 5
<211> LENGTH: 1376
<212> TYPE: DNA
<213> ORGANISM: Rattus norvegicus
<220> FEATURE:
<221> NAME/KEY: CDS
<222> LOCATION: (154)..(708)
<221> NAME/KEY: mat peptide
<222> LOCATION: (433)..(582)

<400> SEQUENCE: 5

```
tccagccttt accgctcctg gtttctcggc ttctcatcgc agtcagtctt ggactttgcg        60
ggttttgccg ctgtcagaag gacgtctcgg actttctgct tcaagtgctt gacaactcac       120
cctttcagca gggtatcgga gcatcgctac aga atg aag ctg gtt tcc atc gcc       174
```

```
                                    Met Lys Leu Val Ser Ile Ala
                                                -90 ctg atg tta ttg ggt tcg ctc gcc gtt ctc ggc gcg gac acc gca cgg      222
Leu Met Leu Leu Gly Ser Leu Ala Val Leu Gly Ala Asp Thr Ala Arg
    -85             -80                 -75 ctc gac act tcc tcg cag ttc cga aag aag tgg aat aag tgg gcg cta      270
Leu Asp Thr Ser Ser Gln Phe Arg Lys Lys Trp Asn Lys Trp Ala Leu
-70             -65                 -60                 -55 agt cgt ggg aag agg gaa cta caa gcg tcc agc agc tac cct acg ggg      318
Ser Arg Gly Lys Arg Glu Leu Gln Ala Ser Ser Ser Tyr Pro Thr Gly
                -50                 -45                 -40 ctc gtt gat gag aag aca gtc ccg acc cag act ctt ggg ctc cag gac      366
Leu Val Asp Glu Lys Thr Val Pro Thr Gln Thr Leu Gly Leu Gln Asp
            -35                 -30                 -25 aag cag agc acg tct agc acc cca caa gcc agc act cag agc aca gcc      414
Lys Gln Ser Thr Ser Ser Thr Pro Gln Ala Ser Thr Gln Ser Thr Ala
    -20                 -15                 -10 cac att cga gtc aaa cgc tac cgc cag agc atg aac cag ggg tcc cgc      462
His Ile Arg Val Lys Arg Tyr Arg Gln Ser Met Asn Gln Gly Ser Arg
    -5              -1   1                  5                  10 agc act gga tgc cgc ttt ggg acc tgc aca atg cag aaa ctg gct cac      510
Ser Thr Gly Cys Arg Phe Gly Thr Cys Thr Met Gln Lys Leu Ala His
                15                  20                  25 cag atc tac cag ttt aca gac aaa gac aag gac ggc atg gcc ccc aga      558
Gln Ile Tyr Gln Phe Thr Asp Lys Asp Lys Asp Gly Met Ala Pro Arg
            30                  35                  40 aac aag atc agc cct caa ggc tat ggc cgc cgg cgc cgg cgt tcc ctg      606
Asn Lys Ile Ser Pro Gln Gly Tyr Gly Arg Arg Arg Arg Ser Leu
        45                  50                  55 cca gag gtc ctc cga gcc cgg act gtg gag tcc tcc cag gag cag aca      654
Pro Glu Val Leu Arg Ala Arg Thr Val Glu Ser Ser Gln Glu Gln Thr
    60                  65                  70 cac tca gct cca gcc tcc ccg gcg cac caa gac atc tcc aga gtc tct      702
His Ser Ala Pro Ala Ser Pro Ala His Gln Asp Ile Ser Arg Val Ser
75                  80                  85                  90 agg tta taggtgcggg tggcagcatt gaacagtcgg gcgagtatcc cattggcgcc       758
Arg Leu tgcggaatca gagagcttcg caccctgagc ggactgagac aatcttgcag agatctgcct    818
ggctgcccct aggggaggca gaggaaccca agatcaagcc aggctcacgt cagaaaccga    878
gaattacagg ctgatactct ctccgggcag gggtctgagc cactgccttg cccgctcata    938
aactggtttt ctcacggggc atacggctca ttacttactt gaactttcca aaacctagcg    998
aggaaaagtg caatgcttgt tatacagcca aagtaactca tcatatttaa gtttgttgat  1058
gtcaagaggt ttttttttt gtaacttcaa atatatagaa atattttgt acgttatata    1118 ttgtattaag ggcattttaa agcgattata ttgtcacctt cccctatttt aagaagtgaa  1178
tgtctcagca aggtgtaagg ttgtttggtt ccgtgtgtgt gtgtgtgtgt gtgtgtgtgt  1238
gtgtgtgtgt gtgtgtgtaa ggtggagagc gcctgattac cgcctgtgga tgaagaaaaa  1298
acattgtgtc ttctataatc tatttacata aaatatgtga tctgggaaaa agcaaaccaa  1358
taaactgtct caatgctg                                                 1376

<210> SEQ ID NO 6
<211> LENGTH: 185
<212> TYPE: PRT
<213> ORGANISM: Rattus norvegicus

<400> SEQUENCE: 6
```

-continued

```
Met Lys Leu Val Ser Ile Ala Leu Met Leu Leu Gly Ser Leu Ala Val
            -90             -85                 -80

Leu Gly Ala Asp Thr Ala Arg Leu Asp Thr Ser Ser Gln Phe Arg Lys
            -75             -70                 -65

Lys Trp Asn Lys Trp Ala Leu Ser Arg Gly Lys Arg Glu Leu Gln Ala
        -60             -55                 -50

Ser Ser Ser Tyr Pro Thr Gly Leu Val Asp Glu Lys Thr Val Pro Thr
-45                 -40                 -35                 -30

Gln Thr Leu Gly Leu Gln Asp Lys Gln Ser Thr Ser Ser Thr Pro Gln
            -25                 -20                 -15

Ala Ser Thr Gln Ser Thr Ala His Ile Arg Val Lys Arg Tyr Arg Gln
            -10              -5                  -1   1

Ser Met Asn Gln Gly Ser Arg Ser Thr Gly Cys Arg Phe Gly Thr Cys
  5                  10                  15

Thr Met Gln Lys Leu Ala His Gln Ile Tyr Gln Phe Thr Asp Lys Asp
 20              25                  30                  35

Lys Asp Gly Met Ala Pro Arg Asn Lys Ile Ser Pro Gln Gly Tyr Gly
             40                  45                  50

Arg Arg Arg Arg Arg Ser Leu Pro Glu Val Leu Arg Ala Arg Thr Val
             55                  60                  65

Glu Ser Ser Gln Glu Gln Thr His Ser Ala Pro Ala Ser Pro Ala His
         70                  75                  80

Gln Asp Ile Ser Arg Val Ser Arg Leu
         85                  90
```